United States Patent [19]

Burzynski

[11] Patent Number: 5,254,587
[45] Date of Patent: Oct. 19, 1993

[54] METHODS FOR TREATING AIDS

[76] Inventor: Stanislaw R. Burzynski, 20 W. Rivercrest, Houston, Tex. 77042

[21] Appl. No.: 790,584

[22] Filed: Nov. 8, 1991

Related U.S. Application Data

[62] Division of Ser. No. 577,464, Sep. 4, 1990, Pat. No. 5,089,508.

[51] Int. Cl.$^5$ .......................................... A61K 31/195
[52] U.S. Cl. .................................. 514/563; 514/534; 514/546; 514/552; 514/567; 514/570
[58] Field of Search ............... 514/534, 546, 552, 563, 514/567, 570

[56] References Cited

U.S. PATENT DOCUMENTS

| | | | |
|---|---|---|---|
| 4,558,057 | 12/1985 | Burzynski | 514/328 |
| 4,605,647 | 8/1986 | Lavielle et al. | 514/85 |
| 4,705,796 | 11/1987 | Hendry et al. | 514/328 |
| 4,835,151 | 5/1989 | Gittos | 514/728 |
| 4,940,705 | 7/1990 | Boshagen et al. | 514/227.8 |
| 4,990,537 | 2/1991 | Okuyama et al. | 514/634 |
| 5,098,906 | 3/1992 | Sircar et al. | 514/262 |
| 5,110,600 | 5/1992 | Green | 424/45 |

OTHER PUBLICATIONS

Kreutzberger et al., 82 CA: 3853j, 1975.
Kloecking et al., 91 CA: 158192c, 1979.
Burzynski, S. R. et al., "Preclinical Studies on Antineoplaston AS2-1 and Antineoplaston AS2-5," CA 105:164561W (1986).

(List continued on next page.)

*Primary Examiner*—Frederick E. Waddell
*Assistant Examiner*—Russell Travers
*Attorney, Agent, or Firm*—Arnold, White & Durkee

[57] ABSTRACT

The present invention provides methods for treating AIDS-related diseases by administering to an afflicted host pharmaceutical compositions containing a therapeutically effective amount of substituted piperidinedione of the formula

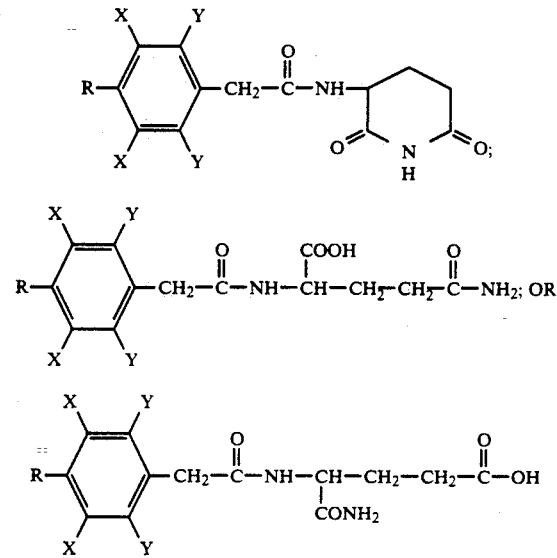

or mixtures thereof,
wherein
R is OH, NH$_2$, OW, or H;
X is H, F, Cl, Br, I, OH, OW, NO$_2$, or NH$_2$;
Y is H, F, Cl, Br, or I;
W is

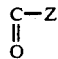

or a C$_1$ to C$_{12}$ aliphatic group;
Z is an aliphatic or aromatic group of C$_1$ to C$_{12}$;
X and Y can both vary within the compound; and pharmaceutically acceptable salts thereof.

The pharmaceutical compositions further may include R,X,Y substituted phenylacetic acid.

9 Claims, No Drawings

OTHER PUBLICATIONS

Ashraf, A. Q. et al., "Preclinical Studies on Antineoplaston A10 Injections," CA 105:164562X (1986).

Lehner, A. F. et al., "3-Phenylacetylamino-2,6-Piperidinedione, A Naturally-Occurring Peptide Analogue with Apparent Antineoplastic Activity, May Bind to DNA," Drugs Exptl. Clin. Res. Suppl. 1, 12:57-72 (1986).

Hendry, L. B. et al., "Stereochemical Modelling Studies of the Interaction of Antineoplaston A10 with DNA," Drugs Exptl. Clin. Res. Suppl. 1, 13:77-81 (1987).

Burzynski et al., "Purification, Structure Determination, Synthesis and Animal Toxicity Studies of Antinepolaston A10," 13th International Congress of Chemotherapy, pp. 1-11 (1983).

Burzynski, "Isolation, Purification, and Synthesis of Antineoplastons," International Journal of Experimental and Clinical Chemotherapy, pp. 63-69 (1989).

METHODS FOR TREATING AIDS

This application is a division of application Ser. No. 07/577,464 filed Sep. 4, 1990, and issued as U.S. Pat. No. 5,089,508 on Feb. 18, 1992.

The present invention relates to the prevention and treatment of diseases caused by retroviruses, particularly AIDS (Acquired Immune Deficiency Syndrome), ARC (AIDS-related complex), and PGL (Persistent Generalized Lymphadenopathy).

BACKGROUND OF THE INVENTION

The AIDS epidemic is traced back to the Jun. 5, 1981 volume of *Mortality and Morbidity Weekly Report* which contains a description by Michael Gottlieb of five cases of Pneumocystis carinii pneumonia in homosexual men. (CDC., MMWR 30:250 (1981)) After the information of additional cases of severe immunosuppression in young men accumulated, the disease became known as "Acquired Immune Deficiency Syndrome". Since the discovery of this syndrome, over 130,000 Americans have been diagnosed with AIDS and over 80,000 died.

One of the most interesting features of dysfunction of the immune system in individuals suffering from AIDS is decreased T4 lymphocyte count and increased T8 lymphocyte count resulting in reverse ratio of T4 and T8 cells (helper/suppressor ratio). The main efforts in the initial study of the disease concentrated on the isolation of the causative agent. The discovery of such agent called "HTLV-III" was initially announced by Robert Gallo of the National Cancer Institute (Gallo et al., *Science*, 220:865 (1983)). Approximately at the same time, a group of French researchers, headed by Luc Montagnier, reported isolation of Lymphadenopathy Associated Virus (LAV). These two newly discovered viruses were found to be identical and since 1986 have been officially called Human Immunodeficiency Virus (HIV). In spite of the fact that a majority of scientists believe that AIDS is caused by HIV, some researchers have produced evidence that HIV is not a causative agent (*Duesberg Proc. Natl. Acad. Sci. U.S.A.*, 86:755 (1989)). The researcher credited with discovery of HIV now believes that mycoplasma helps the virus to produce the disease (Montagnier, *Res. Virol.*, b *141:5* (1990)).

Regardless what the causative agent is, a common consent among the researchers is that AIDS is a disease characterized by progressive dysfunction of the immune system. T4 and T8 lymphocytes, which are the affected cells of the immune system, develop according to the program encoded in the DNA of the cell. In an HIV infected cell, the program in DNA also contains the fragment corresponding to viral RNA, which was transcribed through reverse transcriptase. The presence of such a program causes the T4 cell to malfunction and live a much shorter life and T8 cells to multiply more rapidly The decrease of T4 lymphocyte count and increase of T8 lymphocyte count will cause progressive failure of the immune system manifested by opportunistic infections and neoplastic diseases associated with AIDS, ultimately leading to the patient's death.

So far, no cure for AIDS has been found. Most of the therapeutic approaches are employing antiviral therapy, such as zidovudine (AZT). The treatment representing this invention is based upon cell differentiating agents, termed antineoplastons.

The present inventor postulates that the human body possesses a biochemical defense system consisting of antineoplastons, which are small and medium size peptides and amino acid derivatives (Burzynski, *Internat. J. Exp. Clin. Chemother.*, 2:63 (1989)). The basis of defense in this system is reprogramming of the cells which contain the wrong program for development. Such theory has been tested in the treatment of cancer by inducing normal differentiation in cancer cells (Burzynski, U.S. Pat. Nos. 4,470,970, 4,558,057 and 4,559,325).

Antineoplaston A10 was the first active ingredient isolated and synthetically produced (Burzynski et al., *Proc. 13 Internat. Cong. Chemother., Vienna, Austria*, 17:P.S.12.4.11-4) Antineoplaston A10, which chemically is 3-phenylacetylamino-2,6-piperidinedione, undergoes enzymatic hydrolysis in human intestine to form phenylacetylglutamine and phenylacetylisoglutamine in the ratio of 4:1. Pharmaceutical formulations of the two digestion products of Antineoplaston A10 was named Antineoplaston A10 injections (Burzynski, *Internat. Journal Exp. Clin. Chemother.*, 2:63 (1989). See also U.S. Pat. Nos. 4,470,970, 4,558,057 and 4,559,325). Acid hydrolysis of Antineoplaston A10 initially produces phenylacetylglutamine and phenylacetylisoglutamine. When hydrolysis is carried further, the products of reaction include phenylacetic acid, glutamic acid and ammonia. The sodium salt of phenylacetylglutamine was named Antineoplaston AS2-5 and the mixture of the sodium salts of phenylacetylglutamine and phenylacetic acid in the ratio of 1:4 was named Antineoplaston AS2-1 (Burzynski, *Internat. Journal Exp. Clin. Chemother.*, 2:63 (1989)).

SUMMARY OF THE INVENTION

The present invention provides methods for treating AIDS-related diseases using a pharmaceutical composition containing a therapeutically effective amount of a piperidinedione compound of the formula

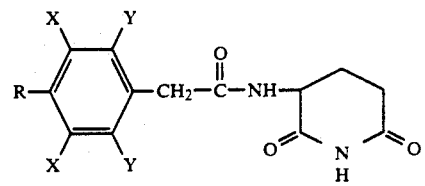

wherein
R is OH, $NH_2$, OW, or H;
X is H, F, Cl, Br, I, OH, OW, $NO_2$ or $NH_2$;
Y is H, F, Cl, I or Br;
W is

or a $C_1$ to $C_{12}$ aliphatic group;
Z is an aliphatic or aromatic group of from $C_1$ to $C_{12}$;
X and Y can both vary within the compound; and pharmaceutically acceptable salts thereof. Also useful for the treatment of AIDS-related diseases are pharmaceutical compositions containing as an active ingredient the hydrolysis products of formula [I] piperidinediones, namely R,X,Y substituted phenylacetylglutamine; R,X,Y substituted phenylacetylisoglutamine; R,X,Y substituted phenylacetic acid; mixtures thereof; and pharmaceutically acceptable salts thereof.

As used herein, "pharmaceutically acceptable salts" mean salts having the biological activity of the parent compound and lacking unusually toxic activity at the selected administration level. Such salts include inorganic sodium, potassium and ammonium salts, organic diethanolamine, cyclohexylamine, and amino acid salts.

AIDS-related diseases include AIDS, ARC, PGL and AIDS-related tumors.

Antineoplaston AS2-1 (1:4 ratio of sodium salt of phenylacetylglutamine and sodium salt of phenylacetic acid) has been administered for the purpose of treating AIDS-related diseases in the form of 500 mg capsules and 100 mg/ml intravenous infusions. Antineoplaston A10 100 mg/ml (4:1 ratio of phenylacetylglutamine sodium salt and phenylacetylisoglutamine sodium salt) intravenous infusions have also been used in the treatment of AIDS-related diseases and AIDS-related tumors.

DETAILED DESCRIPTION OF THE PREFERRED EMBODIMENTS

I. Methods of Preparing Piperidinediones

The piperidinedione compounds of this invention can be prepared by condensation of the appropriate R,X,Y substituted phenylacetic acid derivative with L-glutamine to produce the corresponding R,X,Y substituted phenylacetylglutamine derivative that is then intramolecularly cyclized to the desired 3-(N-R,X,Y substituted phenylacetylamino)-2,6-piperidinedione. The condensation reaction is facilitated by prior activation of the phenylacetic acid derivative with a reagent such as N-hydroxysuccinimide in the presence of DCC (N,N-dicyclohexylcarbodiimide), 2-mercaptothiazoline in the presence of DCC, or DCC alone. The phenylacetylglutamine derivative is also preferably activated before cyclization by reaction with N-hydroxysuccinimide in the presence of DCC or by reaction with 1,1'-carbonyldiimidazole. These reactions are described in more detail in Burzynski, *Drugs of the Future*, 10(2):103 (1985).

Desired R,X,Y substituted derivatives of phenylacetic acid can be purchased commercially or prepared synthetically by methods known to those skilled in the art according to well established rules of electrophilic and nucleophilic aromatic substitution. For example, 4-hydroxyphenylacetic acid, which is commercially available from Aldrich Chemical Company, Inc., can be nitrated with dilute $HNO_3$ to produce 4-hydroxy-3-nitrophenylacetic acid that is used as is in the next step of reaction. Alternatively, the nitro group in 4-hydroxy-3-nitrophenylacetic acid can be reduced to the corresponding amine and then reacted with sodium nitrite in acid to form the diazonium salt, that can be converted into a wide range of functional groups, including chloro, fluoro, bromo and hydroxyl. Phenylacetic acid can alternatively be nitrated in the 4-position to produce 4-nitrophenylacetic acid, that is used as is in the reaction or converted to the diazonium salt and derivatized. The nitro group can be reduced to the corresponding amino group as a final step of reaction by methods known to those skilled in the art, including catalytic hydrogenation.

Prodrugs of the hydroxyl or amino derivatives of 3-N-phenylacetylamino-2,6-piperidinedione can be prepared by alkylation or acylation of the hydroxyl or amino moieties according to established methods. These protecting groups can be cleaved in vivo or in vitro by the appropriate enzyme, generating the active compound.

II. Preparation of Pharmaceutical Compositions and Mode of Administration

As stated above, the R,X,Y substituted piperidinediones, R,X,Y substituted phenylacetic acid, and R,X,Y substituted phenylacetylglutamine of the present invention are useful in the treatment of AIDS-related diseases. Pharmaceutical compositions, including these active compounds, can be prepared as described below.

The active compound, mixtures of the active compounds, or pharmaceutically acceptable salts thereof, are included in the pharmaceutically acceptable carrier or diluent in an amount sufficient to exert a therapeutic effect, i.e., increasing T4 cell count and decreasing T8 cell count. The active materials can be administered by any appropriate route, for example, orally, parenterally, intravenously, intradermally, subcutaneously, intraperitoneally, or topically, in liquid or solid form.

The active compound is included in the pharmaceutically acceptable carrier in an amount sufficient to exert a therapeutically useful effect on the AIDS-diseased patient without serious toxic effect. The therapeutic effect is measured by an increasing T4 cell count, decreasing T8 cell count, and increasing T4/T8 ratio. Normal values for T4 cell count range from $450/mm^3$ to $1300/mm^3$. Normal values for T8 cell count are from $250/mm^3$ to $750/mm^3$. Normally, the T4/T8 ratio is more than 0.9.

The concentration of active compound in the drug composition will depend upon absorption, inactivation, and excretion rates of the active compound as well as other factors known to those skilled in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The active ingredient may be administered at once, or may be divided into a number of smaller doses to be administered at varying intervals of time. For less advanced cases of HIV infection and AIDS, we are using treatment orally. Typically, the patient is given Antineoplaston AS2-1 capsules from 3 to 10 g/day, or 40 mg/kg/24 h to 150 mg/kg/24 h, and preferably, 6 g/day or 85 mg/kg/24 h. Antineoplaston A10 capsules (3-phenylacetylamino-2,6-piperidinedione) can be given from 3 g to 14 g/day or 40 mg/kg/24 h to 200 mg/kg/24 h, preferably 6 g/day or 85 mg/kg/24 h. The dosages of sodium salt phenylacetylglutamine given orally will be five times smaller than AS2-1 capsules, because AS2-1 consists of sodium salts of phenylacetylglutamine (1 part) and phenylacetic acid (4 parts).

For advanced cases of AIDS, we are using treatment in the form of intravenous infusions. The dosages for sodium salt phenylacetylglutamine are from 2.0 g to 120 g/day, preferably 70 g/day. The dosages for phenylacetylisoglutamine are from 2.0 g to 30 g/day, preferably 14 g/day. The dosages for intravenously administered sodium salt of phenylacetic acid are from 8.0 g to 40 g/day, preferably 24 g/day.

If oral administration is desired, although not required, the compound may be provided in a composition that protects it from the acidic environment of the stomach. The compound can be orally administered in combination with an antacid formulation. The composition can also be administered in an enteric coating that maintains its integrity in the stomach and releases the active compound in the intestine.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, capsules, elixirs, suspensions, syrups or the like. Pharmaceutically compatible binding agents and/or adjuvant materials can be included as part of the composition.

The active compounds can also be mixed with other active materials that do not impair the desired action, or with materials that supplement the desired action, including other HIV antiviral agents such as AZT.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

The following examples illustrate the present invention in further detail.

EXAMPLE 1 (PATIENT: GM)

The patient is a 34-year-old white male who complained of recurrent infections. The patient was practicing homosexual lifestyle. This patient was in reasonable health until January 1989 when he was found to be HIV positive. The symptoms of the disease he had since then were recurrent upper respiratory infections and Herpes zoster infection in January 1990. In August 1989, he began treatment with zidovudine. After initial improvement, his T4 cell count began to decrease (from 741/mm$^3$ on Dec. 12, 1989 to 608/mm$^3$ on Mar. 6, 1990 and 420/mm$^3$ on Apr. 23, 1990). T8 cell count, after initial decrease, continued to increase. His T8 cell count on Dec. 12, 1989 was 836/mm$^3$ and 969/mm$^3$ on Mar. 6, 1990 and 1420/mm$^3$ on Apr. 23, 1990. After initial increase, T4/T8 ratio began to decrease (0.88 on Dec. 12, 1989, 0.62 on Mar. 6, 1990 and 0.30 on Apr. 23, 1990).

The patient began treatment with Antineoplaston AS2-1, 500 mg capsules on Apr. 20, 1990 and was advised to take three capsules four times daily with meals (1.5 g four times daily). He did not suffer any side effects and was feeling well during the course of treatment. The follow-up evaluation on May 21, 1990 and May 29, 1990 revealed continuous increase of T4 cell count (420/mm$^3$ on Apr. 23, 1990, 450/mm$^3$ on May 21, 1990 and 480/mm$^3$ on May 29, 1990). T8 cell count continued to decrease (1420/mm$^3$ on Apr. 23, 1990, 1080/mm$^3$ on May 21, 1990, 848/mm$^3$ on May 29, 1990). T4/T8 ratio continues to increase (0.30 on Apr. 23, 1990, 0.42 on May 21, 1990, 0.56 on May 29, 1990). Normal values for T8 count are from 250/mm$^3$ to 750/mm$^3$ and T4/T8 ratio is more than 0.9. The continuous increase of T4 cell count, decrease of T8 cell count and increase of T4/T8 ratio indicates objective improvement.

During the treatment with Antineoplaston AS2-1, the patient continued to take zidovudine at the same dosages as before the treatment with Antineoplaston AS2-1. Since he had continuous worsening while taking zidovudine before, it is not expected that zidovudine was instrumental in obtaining objective improvement.

EXAMPLE 2 (PATIENT: LM)

The patient is a 29-year-old male who was complaining of shortness of breath, cough, night sweats, fever and loss of 25 pounds of weight within three weeks before coming under my treatment.

This patient was in good health until the beginning of April 1990 when he was diagnosed with Hodgkin's disease of mixed cellularity. The diagnosis was based upon the biopsy of the cervical lymph node. The patient was found to have enlargement of liver and spleen and multiple lymph nodes in the neck, chest and the abdomen. The bone marrow biopsy was highly suggestive of involvement with Hodgkin's disease. The laboratory test done at the beginning of the treatment for Hodgkin's disease indicated HIV infection which prompted the final diagnosis of Hodgkin's disease, stage IV associated with AIDS. The patient associated his HIV infection with intravenous use of narcotics. He did not receive any previous treatment for AIDS and Hodgkin's disease.

This patient began the treatment with Antineoplaston A10, 100 mg/ml intravenous infusions on Apr. 23, 1990. The dose of the formulation was gradually increased to 70g IV daily. On Apr. 27, 1990, Antineoplaston AS2-1, 100 mg/ml infusions were added to the treatment and the dosage of this formulation was gradually increased to 20g/24h. The treatment was given in the form of continuous infusions through ambulatory pump. The complete evaluation performed on Jun. 22, 1990 revealed marked improvement in the patient's condition. The patient was feeling very well and did not have any complaints. The liver and spleen were no longer enlarged by physical examination. The laboratory tests on May 17, 1990 revealed T4 cell count of 82/mm$^3$ The repeated test on Jun. 4, 1990 revealed marked increase of T4 cell count to 133/mm$^3$. The increase of T4 cell count indicates improvement in the treatment of AIDS.

EXAMPLE 3 (PATIENT: RH)

The patient is a 32-year-old white male who was complaining of fever and night sweats. This patient was in good health until approximately 1985 when he was diagnosed as HIV positive. He did not use intravenous drugs, and most likely, his infection was due to homosexual contact. He did not have any treatment until Jun. 8, 1990 when he was started on zidovudine. Before beginning the treatment with Antineoplaston AS2-1, his T4 cell count was decreasing and T8 cell count was increasing.

The patient began treatment with Antineoplaston AS2-1, 500 mg capsules on Jun. 11, 1990. The patient was advised to take three capsules of Antineoplaston AS2-1 four times daily with meals. The treatment was tolerated very well without side effects. The most recent blood test of Jul. 30, 1990 revealed increase of T4 cell count and decrease of T8 cell count. Helper/suppressor ratio increased. His pre-treatment T4 cell count of Jun. 8, 1990 was 496/mm³ Subsequent T4 cell counts were as follows: 484/mm³ on Jul. 9, 1990 and 546/mm³ on Jul. 30, 1990. Pre-treatment T8 cell count on Jun. 8, 1990 was 2232/mm³. The following T8 cell counts were 1430/mm³ on Jun. 9, 1990 and 1281/mm³ on Jul. 30, 1990. T4/T8 ratio increased from initial 0.22 on Jun. 8, 1990 to 0.33 on Jul. 9, 1990 and 0.42 on Jul. 30, 1990.

What is claimed is:

1. A method of treating AIDS in an afflicted host comprising:

administering to the host a pharmaceutical composition containing a therapeutically effective amount of an active compound of the formula:

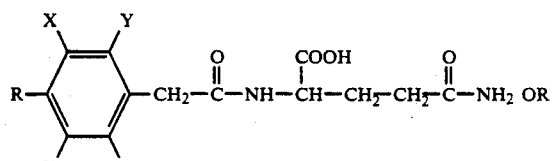

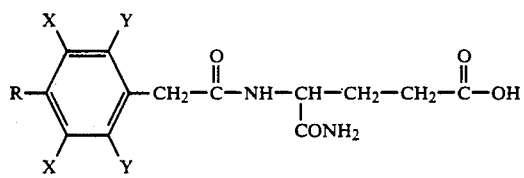

or mixtures thereof,
wherein
R is OH, NH₂, OW, or H;
X is H, F, Cl, Br, I, OH, OW, NO₂, or NH₂;
Y is H, F, Cl, Br, or I;
W is

or a $C_1$ to $C_{12}$ aliphatic group;
Z is an aliphatic or aromatic group of $C_1$ to $C_{12}$;
X and Y can both vary within the compound; and pharmaceutically acceptable salts thereof.

2. The method of claim 1 wherein the pharmaceutical composition contains as an active compound phenylacetylglutamine, phenylacetylisoglutamine, mixtures thereof, or pharmaceutically acceptable salts thereof.

3. The method of claim 1 wherein the pharmaceutical composition contains a 4:1 ratio of phenylacetylglutamine and phenylacetylisoglutamine.

4. The method of claim 1 wherein the active compound is administered orally, topically or by injection.

5. The method of claim 1 wherein the pharmaceutical composition further includes an active compound of the formula:

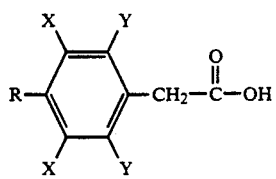

wherein
R is OH, NH₂, OW, or H;
X is H, F, Cl, Br, I, OH, OW, NO₂, or NH₂;
Y is H, F, Cl, Br, or I;
W is

or a $C_1$ to $C_{12}$ aliphatic group;
Z is an aliphatic or aromatic group of $C_1$ to $C_{12}$;
X and Y can both vary within the compound; and pharmaceutically acceptable salts thereof.

6. The method of claim 2 wherein the pharmaceutical composition further includes phenylacetic acid or its pharmaceutically acceptable salts.

7. The method of claim 6 wherein the phenylacetylglutamine or phenylacetylisoglutamine and phenylacetic acid are administered in 1:4 ratio.

8. The method of claim 3 wherein the pharmaceutical composition is administered to humans in an amount of from about 40 mg/kg/24 h to about 200 mg/kg/24 h.

9. The method of claim 7 wherein the pharmaceutical composition is administered to humans in an amount of from about 40 mg/kg/24 h to about 150 mg/kg/24 h.

* * * * *